United States Patent [19]

Ogino

[11] Patent Number: 5,412,466
[45] Date of Patent: May 2, 1995

[54] APPARATUS FOR FORMING FLATTENED SAMPLE FLOW FOR ANALYZING PARTICLES

[75] Inventor: Shinichi Ogino, Kobe, Japan

[73] Assignee: Toa Medical Electronics Co., Ltd., Kobe, Japan

[21] Appl. No.: 886,933

[22] Filed: May 22, 1992

[30] Foreign Application Priority Data

Jul. 26, 1991 [JP] Japan .................. 3-210053
Jul. 26, 1991 [JP] Japan .................. 3-210054

[51] Int. Cl.6 ................. G01N 33/48; G01N 21/00
[52] U.S. Cl. ............................... 356/246; 356/39
[58] Field of Search .............. 356/39, 72, 73, 318, 356/417, 246; 435/287, 291, 808; 209/3.1, 579, 906

[56] References Cited

U.S. PATENT DOCUMENTS

| | | | |
|---|---|---|---|
| 4,131,899 | 12/1978 | Christou | 346/140 |
| 4,338,024 | 7/1982 | Bolz et al. | 356/23 |
| 4,550,326 | 10/1985 | Allen et al. | 346/140 |
| 4,756,427 | 7/1988 | Göhde et al. | 209/3.1 |
| 4,988,619 | 1/1991 | Pinkel | 435/808 |
| 5,173,740 | 12/1992 | Fukuda et al. | 356/246 |

Primary Examiner—Robert J. Warden
Assistant Examiner—Theresa T. Snider
Attorney, Agent, or Firm—Jones, Tullar & Cooper

[57] ABSTRACT

An apparatus for forming a flattened sample flow by passing a sample (liquid specimen) containing particle components such as blood and urine, in a broad, thin, flat flow. This apparatus is preferably used in an apparatus for analyzing particle images by emitting a strobe light to a sample flat flow, and taking the still images of the particle components. More specifically, the cross section of a measuring passage of a flow cell is rectangular with a side ratio of one to several times, with a shape that gradually narrows in width only in one direction of the lead-in passage, and the discharge port at the front end of the sample nozzle has a flat opening, or small discharge ports are arranged horizontally in a row. The decreasing direction of the width in the lead-in passage and the shorter diameter direction of the flat discharge port or the direction of the small discharge ports arranged horizontally in a row are matched. Besides, the cross section of the measuring passage of the flow cell is rectangular with a side ratio of one to several times, and sheath liquid dividing means disposed at the discharge port upstream side of the sample nozzle for dividing the sheath liquid into two symmetrical flows. The sample nozzle is placed so that the discharge port may be positioned at the converging region of the sheath liquid. For further enhancing the flatness of the sample flow, a sample nozzle having a flat discharge port, or plural discharge ports disposed horizontally in a row is used.

2 Claims, 18 Drawing Sheets

APPARATUS FOR FORMING FLATTENED SAMPLE FLOW FOR ANALYZING PARTICLES

BACKGROUND OF THE INVENTION

The present invention relates to an apparatus for forming a flattened sample flow for passing a sample (liquid specimen) containing particle components such as blood and urine in a wide, thin, flat flow. The apparatus of the present invention is preferably used in an apparatus for analyzing particle images by emitting a strobe light to the flattened sample flow and taking still images of particle components.

The apparatus for taking images of particle components passed in a flat flow and analyzing particles by image processing is disclosed in Japanese Laid-open Patent Sho. 57-500995 or the U.S. Pat. No. 4,338,024. The flow cell possesses a large aspect ratio passage (ratio of length to width, more than scores of times) in the measuring region, forms a flat sheath flow in the passage, and takes the still images of its sample flat flow by a video camera. The passage dimensions in the imaging region is disclosed as being 100 $\mu$m in width and 5000 $\mu$m in length (the aspect ratio being 50 times). The sheath flow, meanwhile, refers to a flow having the circumference of a suspension of particles covered with a laminar sheath liquid in order to pass the particles by arranging them in one row precisely in the central part of the liquid flow.

On the other hand, the Japanese Laid-open Utility Model Hei. 3-44626 discloses a nozzle divided into plural nozzle openings along the flattening direction with the front end flattened, and a nozzle having a flat discharge opening for use in the cleanliness measurement of a cleanroom used in the manufacture of semiconductors or the like. Certainly, these nozzles are intended to flatten the sample flow, but sheath flow is not used, and they are merely intended to pass a large volume of liquid specimen. With these nozzles alone, the flat flow having a sufficient flatness as required in the present invention (about 10 $\mu$m $\times$ 900 $\mu$m) is not realized.

In U.S. Pat. No. 4,988,619, fins are disposed flatly across the flow chamber, and cylindrical rods are disposed across the flow chamber. These are, however, intended to enhance the orientation (aligning the direction) of flat particles in the flow cytometry, and it is not possible, as in the cases above, to realize the flatness required in the present invention (about 10 $\mu$m $\times$ 900 $\mu$m).

In conventional flow cells disclosed in Japanese Laid-open Patent Sho. 57-500995 and U.S. Pat. No. 4,338,024, the thickness of the passage is about the size of the particles to be analyzed, and the dimensions are also required to be precise. Accordingly, it was difficult to manufacture and was expensive. Also because of the thin thickness, they were easily broken and hard to handle.

In the ordinary flow cytometer, the flow cell with an aspect ratio of the passage of about 1 is used. Using such a flow cell, the above problems are avoided, but flat sample flow is not formed in that state. Besides, in the apparatus disclosed in Japanese Laid-open Utility Model Hei. 3-44626 or U.S. Pat. No. 4,988,619, sufficient flat flow cannot be formed.

In the Flow Cytometry Handbook, Science Forum (1984), pp. 399–400, the force acting on the sample flow is mentioned. FIG. 1 is a diagram reprinted from this publication, showing a plan view of the flow cell part as seen from the flow direction. Comparing the, h, and, v, directions, the force fh in the, h, direction having a larger throttling ratio acts more than the force fv in the, v, direction having a smaller throttling ratio. This is used for arranging the direction of cells in the sample in a specific direction, and it is insufficient for forming a flat sample flow. Meanwhile, supposing the forces acting on the sample flow to be fh, fv, they are expressed as fh:fv= A/a:B/b, with the relation A/a>B/b.

OBJECT AND SUMMARY OF THE INVENTION

It is hence an object of the present invention to present an apparatus capable of forming a flattened sample flow by using a flow cell with the aspect ratio of flow being passage one to several times.

To achieve the above object, in the flow cell lead-in passage, the width of one side of the passage is narrowed, and communicates with the measurement passage. Then the discharge port of the sample nozzle is flattened, or small discharge ports are arranged horizontally in one row. Furthermore, the decreasing width dimension in the lead-in passage and the narrowing width dimension of the sample nozzle discharge are matched, that is, the decreasing width dimension in the lead-in passage and the diameter dimension when the discharge port is flat, or the vertical direction (the direction orthogonal to the arranging direction) when the discharge ports are arranged horizontally in one direction are matched.

An apparatus for forming flattened sample flow for analyzing particles of the present invention comprises:

a flow cell having a gradually narrowed lead-in passage, a narrow measuring passage contiguous to the lead-in passage, a sheath liquid feed port disposed in the lead-in passage, and a discharge port disposed at the downstream side of the measuring passage, and a sample nozzle for discharging sample disposed in the lead-in passage of the flow cell so that the front end may be directed to the measuring passage, wherein the cross section of the measuring passage of the flow cell is rectangular with a side ratio of one to several times, only the width of one direction of the passage is gradually narrowed in the lead-in passage of the flow cell, a discharge port at the front end of the sample nozzle has an open flat configuration, and the sample nozzle is disposed so that the shorter dimension of the discharge port extends in the same direction as the decreasing dimension of the lead-in passage.

In this case, it is desirable that the discharge port of the sample nozzle may have a broader width in the end portion than the width of the central portion. Moreover, instead of the flat shape of the discharge port of the sample nozzle a sample nozzle may be used, which has a plurality of small discharge ports arranged horizontally in one row, and the sample nozzle may be disposed so that the direction of the small discharge ports may be orthogonal to the decreasing dimension of the lead-in passage.

In this case, as an example, there is only one sample flow inlet at the other end of the sample nozzle, and it is divided into plural small passages inside the sample nozzle, and the small discharge ports are arranged in one row.

In this case, the number of small discharge ports of the sample nozzle is an even number, and it is desired to disposed the small discharge ports at symmetrical positions centered around the sample nozzle.

The diameter of the small discharge ports disposed at the end portion is desired to be larger than the diameter of the small discharge ports disposed in the central portion.

In the lead-in passage, since only one side is narrowed in width, the sheath liquid flows only in that direction, and a large force acts toward the inside of the passage, and in the direction in which the width is, a force does not act. That is, the sample throttling (narrowing down) action occurs only in one direction.

The discharge port of the sample nozzle is not circular as in the prior art, has is a flattened circular form, that is, an approximately elliptical form. Accordingly, the sample liquid discharge from the nozzle is formed into an extremely flat sample flow by the synergistic action of the two (the sample throttling action in the one direction only and the flat flow discharged from the nozzle), even in the measuring passage the aspect ratio of which is one to several times. Also in the case of a sample liquid discharged from plural small discharge ports of the sample nozzle, an extremely flat sample flow may be formed.

To further enhance the flatness of the sample flow, the discharge port of the sample nozzle is, for example, flat (approximately elliptical), or small discharge ports may be horizontally arranged in one row. In such a case, the discharge port is arranged so that the longitudinal direction thereof or the direction of the small discharge ports may be identical with the horizontal projecting direction of the sheath liquid dividing means.

As other means, moreover, a sample nozzle is disposed across the lead-in passage. And at the measuring passage side of the sample nozzle, that is, on the downstream side surface, plural small discharge ports are arranged in one row along the axial direction of the nozzle, and at the upstream side of the sample nozzle, dividing means are disposed for dividing the sheath liquid in the same direction as the axial direction of the sample nozzle.

Another apparatus for forming flattened sample flow for analyzing particles of the present invention comprises:
- a flow cell having a gradually narrowed lead-in passage a narrow measuring passage contiguous to the lead-in passage, a sheath liquid feed port disposed in the lead-in passage, and a discharge port disposed at the downstream side of the measuring passage, and
- a sample nozzle for discharging sample disposed in the lead-in passage of the flow cell so that the front end may be directed to the measuring passage, wherein
- the cross section of the measuring passage of the flow cell is rectangular with a side ratio of one to several times,
- sheath liquid dividing means for dividing the sheath liquid symmetrically into two flows is disposed in contact with the sample nozzle, and
- the discharge port of the sample nozzle is positioned in the sheath liquid converging (confluencing) region at the downstream side of the sheath liquid dividing means.

In this case, using the sample nozzle the front end discharge port of which has a flat opening, it is desired to dispose the sample nozzle so that the longitudinal direction of the discharge port and the lateral projecting direction of the sheath liquid dividing means may be identical.

Furthermore, it is desirable to have the discharge port of the sample nozzle broader in width at its end portion than in its central portion.

Moreover, instead of the sample nozzle with the flat shaped discharge port, using a sample nozzle having small discharge ports disposed horizontally in a row, the sample nozzle may be disposed so that the arranged direction of the small discharge port and the lateral projecting direction of the sheath liquid dividing means may coincide.

As an example of this case, there is one sample flow inlet at the other end of the sample nozzle, and it is branched into plural small passages inside the sample nozzle, and the small discharge ports are arranged in a row.

In this case, using an even number of small discharge ports of the sample nozzle, it is desirable to have the small discharge ports at symmetrical positions centered around the sample nozzle.

Furthermore it is desirable to have the diameter of the small discharge ports disposed at the end portion greater than the diameter of the small discharge ports disposed in the central portion.

Another apparatus for forming a flattened sample flow for analyzing particles of the invention comprises:
- a flow cell having a gradually narrowed lead-in passage, a narrow measuring passage contiguous to the lead-in passage, a sheath liquid feed port disposed in the lead-in passage, and a discharge port disposed at the downstream side of the measuring passage, and
- a sample nozzle for discharging sample disposed in the lead-in passage of the flow cell so that the front end may be directed to the measuring passage, wherein
- the cross section of the measuring passage of the flow cell is rectangular with a side ratio of one to several times,
- a sample nozzle is disposed across the flow of the sheath liquid in the lead-in passage,
- a plurality of small discharge ports are disposed horizontally in a row in the sample nozzle so as to open toward the measuring passage,
- sheath liquid dividing means disposed at the upstream side of the small discharge ports of the sample nozzle in contact with the sample nozzle so as to divide the sheath liquid symmetrically into two flows, and
- the sheath liquid dividing means is disposed so that the lateral projecting direction of the sheath liquid dividing means and the axial direction of the sample nozzle may coincide.

In this case, instead of disposing a plurality of small discharge ports in the sample nozzle, a flat (slit) discharge port may be disposed in the sample nozzle.

The sheath liquid is divided into two flows by the sheath liquid dividing means projecting in the lateral direction. When the sheath liquid flows converge (confluence), the sample liquid discharge from the discharge port of the sample nozzle is sandwiched, so that a flat sample flow is formed.

By flattening the discharge port of the sample nozzle or disposing a plurality of small discharge ports horizontally in one row, a further preferred flat sample flow is formed.

Moreover, when disposing the sample nozzle across the lead-in passage, first the sample liquid is led into the nozzle from one end of the nozzle, and is discharged from the other end of the nozzle. The plural small discharge ports or flat discharge ports are disposed from one end of the sample nozzle to the other end, and therefore the supplied sample liquid is discharged from the plural small discharge ports or flat discharge ports, and a preferred flat sample flow is formed together with the action of the sheath liquid dividing means.

DETAILED DESCRIPTION OF THE PREFERRED EMBODIMENTS

Figure 1:
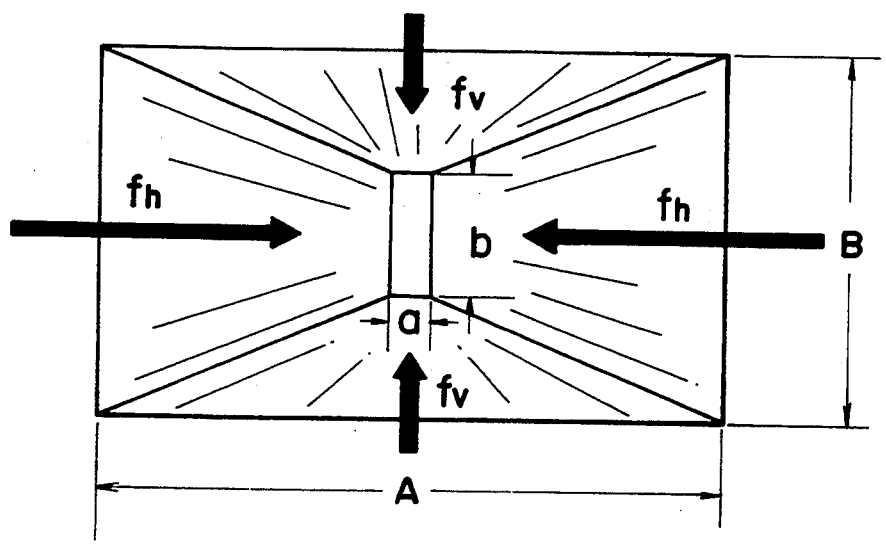
FIG. 1 is an explanatory plan view showing the force acting on the sample flow in a conventional flow cell.

Referring now to the drawings, some of the preferred embodiments of the present invention are described in detail below.

As shown in FIG. 2 to FIG. 9, an apparatus for forming a flattened sample flow for analyzing particles comprises:

a flow cell 10 having a gradually narrowing lead-in passage 14, a narrow measuring passage 16 contiguous to the lead-in passage 14, a sheath liquid feed port 18 disposed to intersect the lead-in passage 14, and a discharge port 20 disposed at the downstream side of the measuring passage 16, and a sample nozzle 12 for discharging sample disposed in the lead-in passage 14 such that the front end of the sample nozzle is directed to the measuring passage 16, wherein the cross section of the measuring passage 16 is rectangular with a side ratio of one to several times, the width of only one direction of the lead in passage 14 is gradually narrowed a discharge port 22 at the front end of the sample nozzle 12 has a flat opening, and the sample nozzle 12 is disposed so that the shorter length of the discharge port 22 may extend in the same direction as the decreasing direction of the lead-in passage 14.

Figure 10:
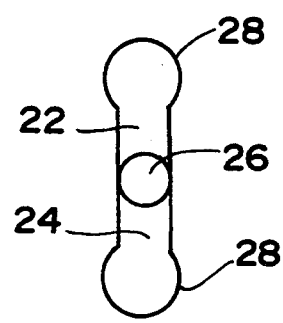
FIG. 10 is an explanatory diagram showing another example of a discharge port of the nozzle shown in FIG. 9.

In the case, as shown in FIG. 10, the construction is such that the discharge port 22 of the sample nozzle 12 may have a broader width in the end portion 28 than the width at the central portion. Moreover, instead of the sample nozzle with a flat shaped discharge part, a sample nozzle 12a may be used, which has a plurality of small discharge ports 30 arranged horizontally in one row, and the sample nozzle 12a may be disposed so that the arranged direction of the small discharge ports 30 may be orthogonal to the decreasing direction of the lead-in passage 14.

In this case, as an example, as shown in FIG. 12 to FIG. 15, there is only one sample flow inlet 26 at the other end of the sample nozzle, and it is divided into plural small passages 36 inside the sample nozzle, with the small discharge ports 30 are arranged in one row.

In the case shown in FIG. 12 to FIG. 15, the number of small discharge ports 30 of the sample nozzle is an even number, and it is desired to disposed the small discharge ports 30 centered symmetrically around the sample nozzle.

The diameter of the small discharge ports disposed at the end portion is desired to be larger than the diameter of the small discharge ports disposed in the central portion.

Since in the lead-in passage 14, the width of one side is narrowed, the sheath liquid flows only in that direction, and a large force acts toward the inside, and in the direction in which the width is, a not changed in width, force does not act. That is, the sample throttling (narrowing down) action occurs only in one direction.

The discharge port 22 of the sample nozzle 12 is not circular as in the prior art, but is in a flattened circular form, that is, an approximately elliptical form. Accordingly, the sample liquid discharge from the nozzle 12 is formed into an extremely flat sample flow by the synergistic action of the two (the sample throttling action in one direction only and the flat flow discharged from the nozzle), even in the measuring passage 16 the aspect ratio of which is one to several times. Also in the case of a sample liquid discharged from plural small discharge ports 30 of the sample nozzle 12a, an extremely flat sample flow may be formed.

Figure 16:
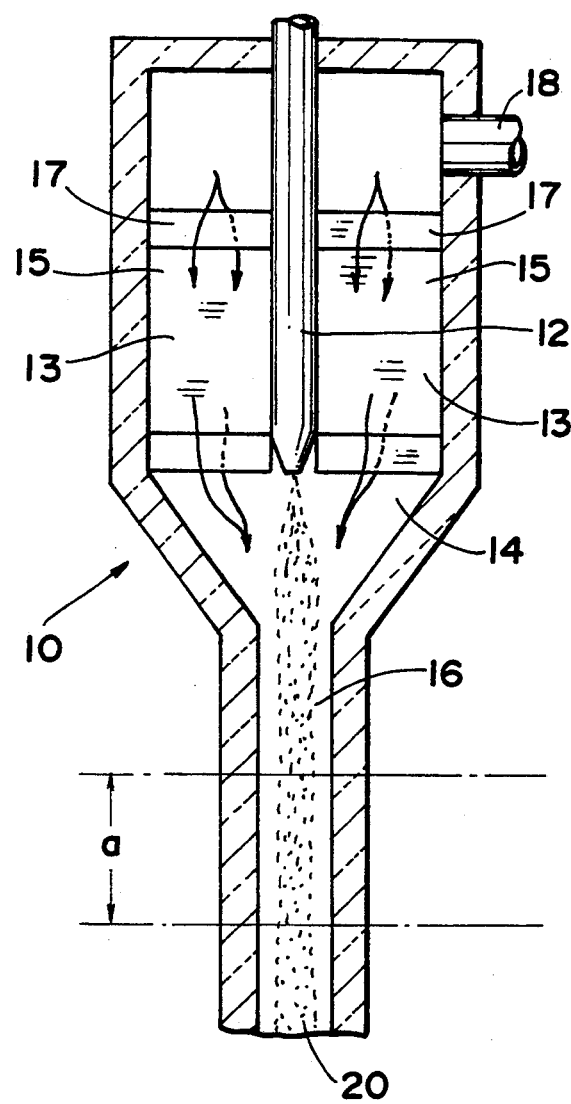
FIG. 16 is a front sectional view showing another embodiment of an apparatus for forming a flattened sample flow for analyzing particles of the present invention.
Figure 17:
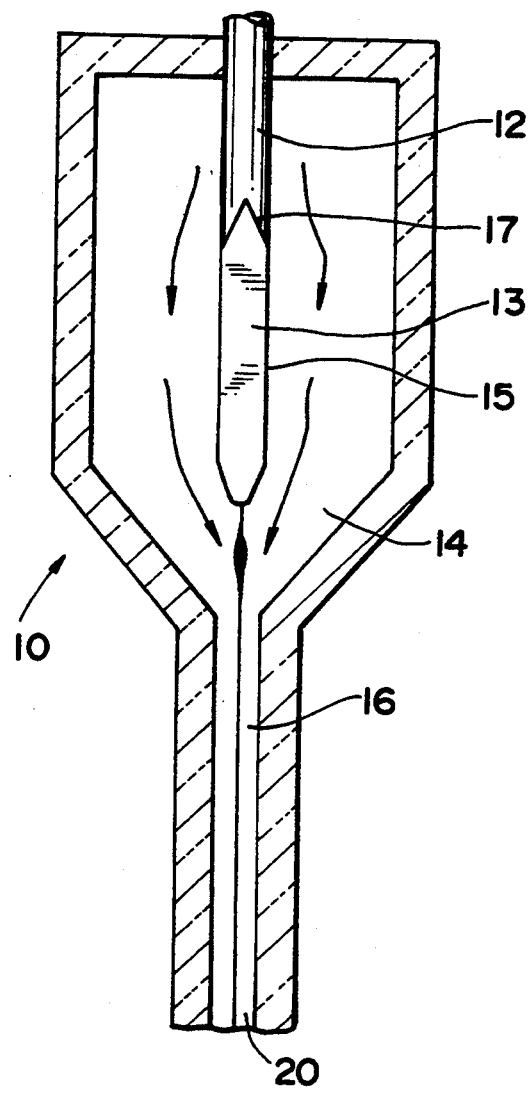
FIG. 17 is a right side sectional view of the apparatus shown in FIG. 16.
Figure 18:
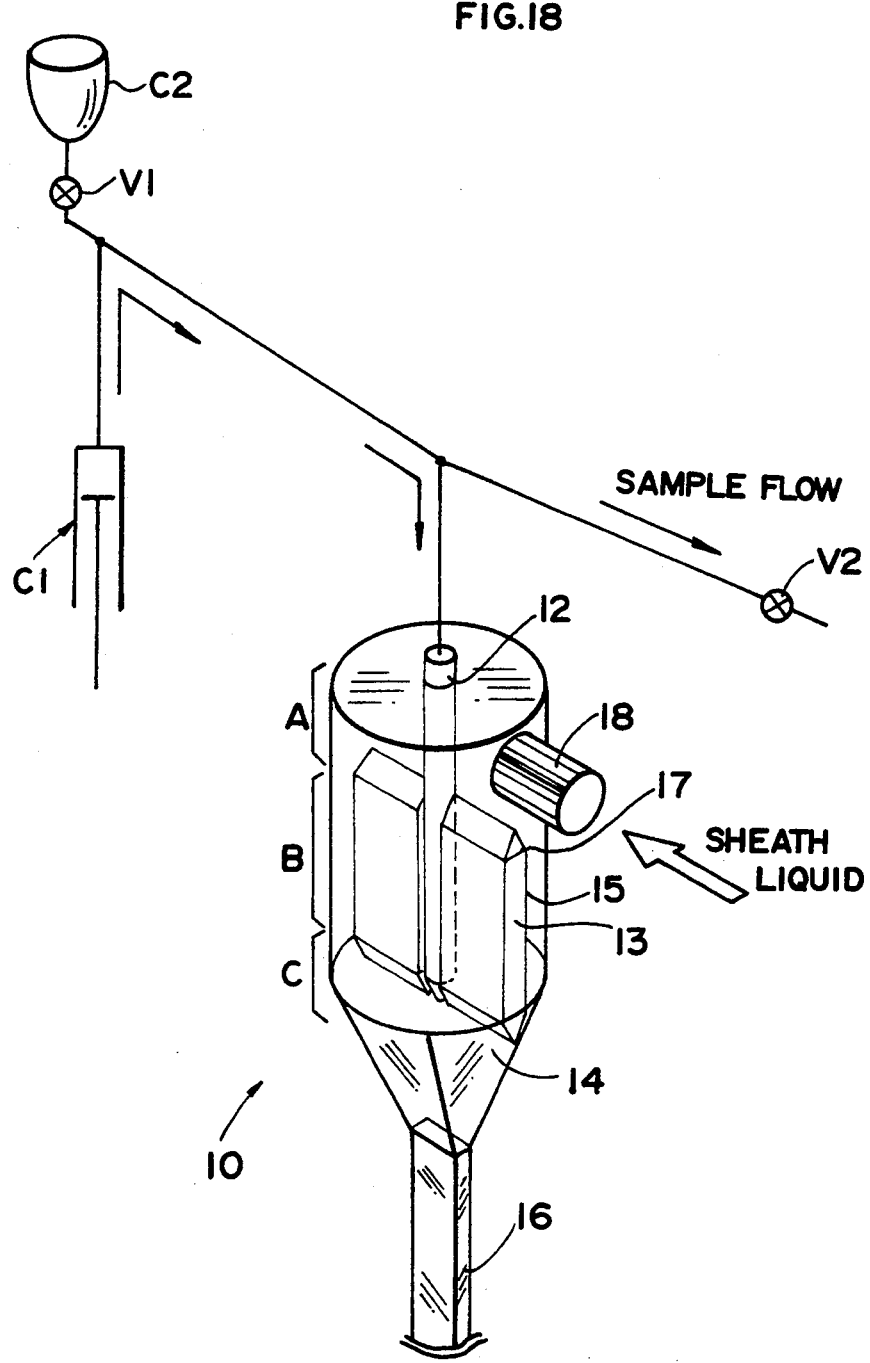
FIG. 18 is a perspective view around the apparatus shown in FIG. 16.

As shown in FIG. 16 to FIG. 18, an apparatus for forming flattened sample flow for analyzing particles comprises:

a flow cell 10 having a gradually narrowing lead-in passage 14, a narrow measuring passage 16 contiguous to the lead-in passage 14, a sheath liquid feed port 18 disposed in the lead-in passage 14, and a discharge port 20 disposed at the downstream side of the measuring passage 16, and a sample nozzle 12 for discharging sample is disposed in the lead-in passage 14 of the flow cell so its front end may be directed to the measuring passage 16, wherein the cross section of the measuring passage 16 of the flow cell 10 is rectangular with a side ratio of one to several times, sheath liquid dividing means 13 for dividing the sheath liquid symmetrically into two flows is disposed in contact with the sample nozzle 12, and the discharge port of the sample nozzle 12 is positioned in the sheath liquid converging (confluencing) region at the downstream side of the sheath liquid dividing means 13.

In this case, as shown in FIG. 5 to FIG. 9, using the sample nozzle 12 the front end discharge port 22 of which is a flat opening, it is desired to dispose the sample nozzle 12 so that the longitudinal direction of the discharge port 22 and the lateral projecting direction of the sheath liquid dividing means 13 may be identical.

Figure 11:
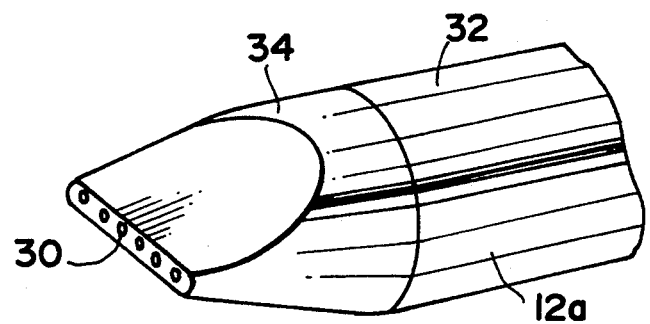
FIG. 11 is a perspective view showing another example of a sample nozzle used in the apparatus of the present invention.

Moreover, instead of the sample nozzle the shaped of the discharge port is flat, as shown in FIG. 11, using a sample nozzle 12a having small discharge ports 30 disposed horizontally in a row, the sample nozzle 12a may be disposed so that the arranging direction of the small discharge ports 30 and the lateral projecting direction of the sheath liquid dividing means 13 may coincide.

As an example of this case, as shown in FIG. 12 to FIG. 15, there is one sample flow inlet 26 at the other end of the sample nozzle, and it is branched into plural small passages 36 inside the sample nozzle, and the small discharge ports 30 are arranged in a row.

As shown in FIG. 24 to FIG. 29, an apparatus for forming a flattened sample flow for analyzing particles comprises:

a flow cell 10 having a gradually narrowing lead-in passage 14, a narrow measuring passage 16 contiguous to the lead-in passage 14, a sheath liquid feed port 18 disposed in the lead-in passage 14, and a discharge port 20 disposed at the downstream side of the measuring passage 16, and a sample nozzle 40 for discharging sample disposed in the lead-in passage 14 of the flow cell so that the front end may be directed to the measuring passage 16, wherein the cross section of the measuring passage 16 of the flow cell 10 is rectangular with a side ratio of one to several times, a sample nozzle 40 is disposed across the flow of the sheath liquid in the lead-in passage 14, a plurality of small discharge ports 42 are disposed horizontally in a row in the sample nozzle 40 so as to open toward the measuring passage 16, sheath liquid dividing means 13 disposed at the upstream side of the small discharge ports 42 of the sample nozzle 40 in contact with the sample nozzle 40 so as to divide the sheath liquid symmetrically into two flows, and sheath liquid dividing means 13 disposed so that the lateral projecting direction of the sheath liquid dividing means 13 and the axial direction of the sample nozzle 40 may coincide.

Figure 30:
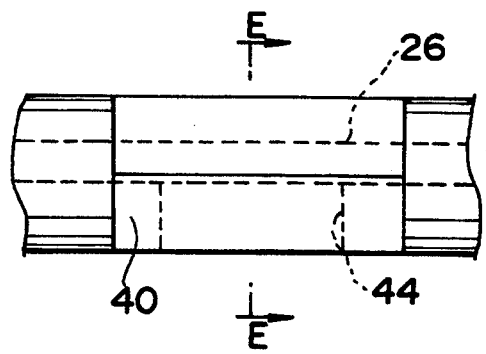
FIG. 30 is a magnified view showing another example of the sample nozzle shown in FIG. 24.
Figure 31:
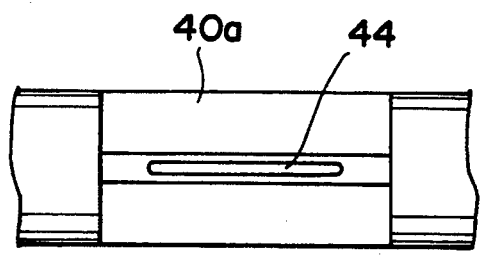
FIG. 31 is a bottom view of the sample nozzle shown in FIG. 30.
Figure 32:
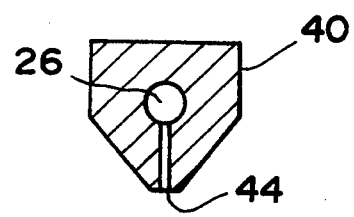
FIG. 32 is an a sectional view along the line E—E in FIG. 30.

In this case, instead of disposing a plurality of small discharge ports 42 in the sample nozzle 40, as shown in FIG. 30 to FIG. 32, a flat (slit) discharge port 44 may be disposed in the sample nozzle 40.

The sheath liquid is divided into two flows by the sheath liquid dividing means 13 projecting in the lateral direction. When the sheath liquid flows converge (confluence), the sample liquid discharge from the discharge port of the sample nozzle 12 is sandwiched, so that a flat sample flow is formed.

By flattening the discharge port of the sample nozzle or disposing a plurality of small discharge ports horizontally in one row, a further preferred flat sample flow is formed.

Moreover, when disposing the sample nozzle 40 across the lead-in passage 14, first the sample liquid is led into the nozzle from one end of the nozzle, and is discharged from the other end of the nozzle. The plural small discharge ports 42 or flat discharge ports 44 are disposed from one end of the sample nozzle to the other end, and therefore the supplied sample liquid is discharged from the plural small discharge ports or flat discharge ports, and a preferred flat sample flow is formed together with the action of the sheath liquid dividing means 13.

Figure 2:
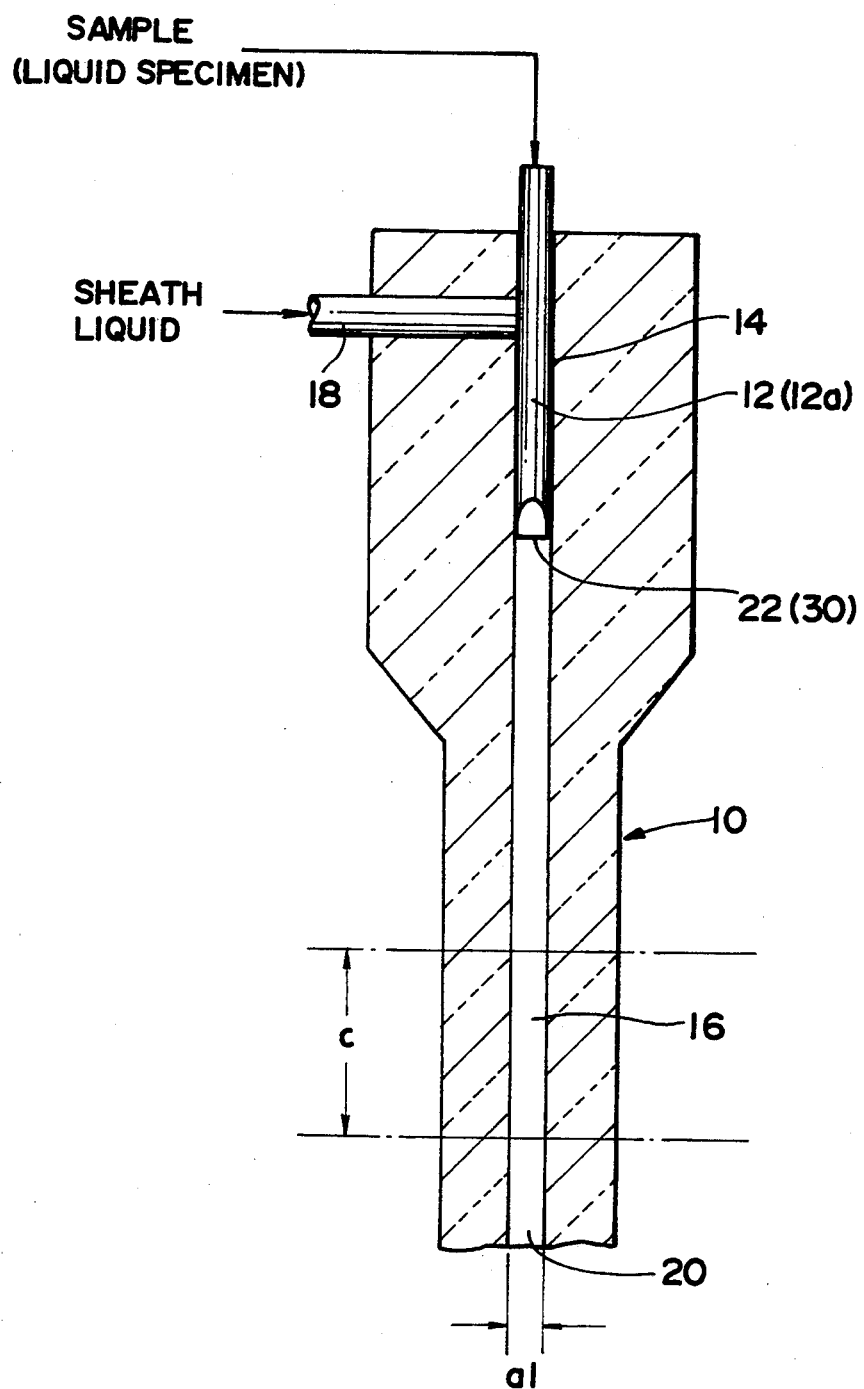
FIG. 2 is a front sectional view showing an embodiment of an apparatus for forming a flattened sample flow for analyzing particles according to the present invention.
Figure 3:
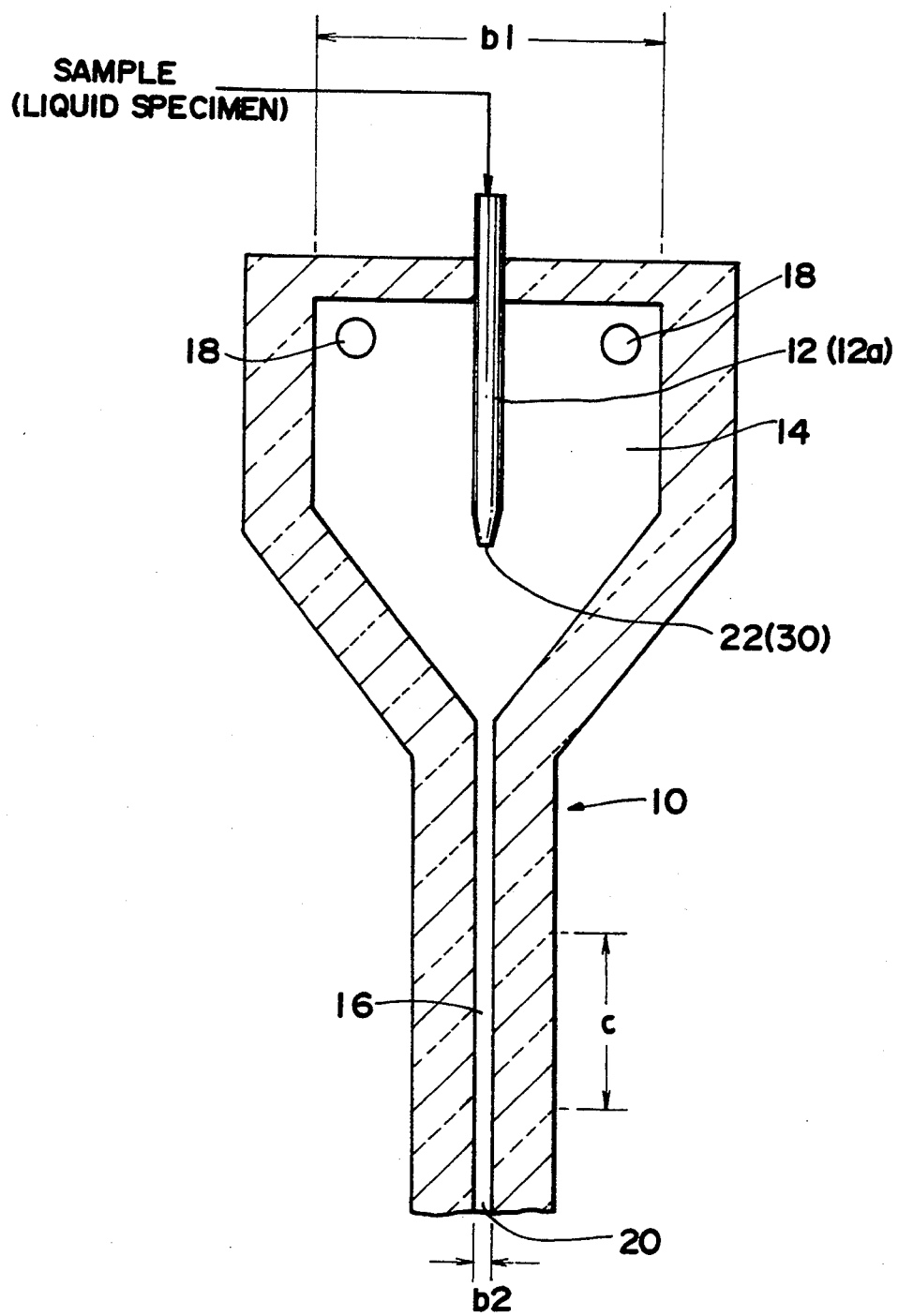
FIG. 3 is a right sectional view of the apparatus shown in FIG. 2.
Figure 4:
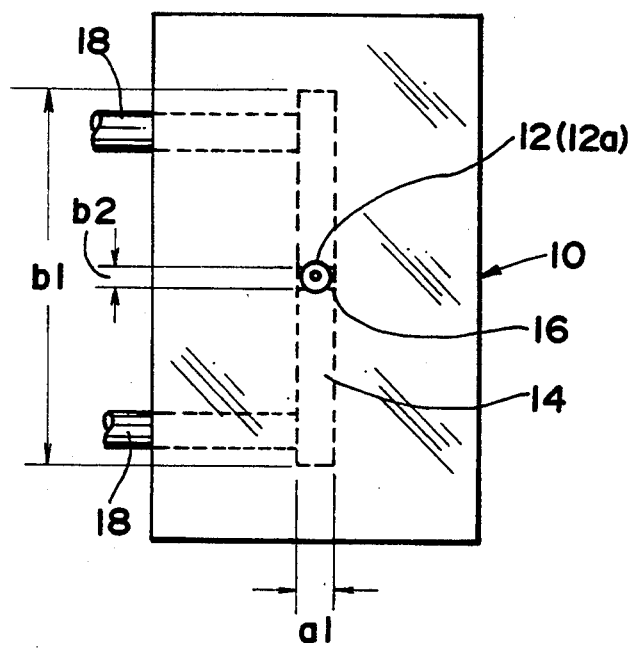
FIG. 4 is a plan view of the apparatus shown in FIG. 2.

FIG. 2 to FIG. 4 relate to an apparatus for forming a flattened sample flow of the present invention. The apparatus comprises a flow cell 10 for forming a sheath flow, and a sample nozzle 12 which is a thin pipe for discharging the sample.

The flow cell 10 is made of transparent material such as glass and plastic, and comprises a lead-in passage 14 gradually narrowed in width in one direction only, a narrow measuring passage 16 contiguous to the lead-in passage 14, a sheath liquid feed port 18 disposed in the lead-in passage 14, and a discharge port 20 disposed at the downstream side of the measuring passage 16. The cross section of the measuring passage 16 is rectangular, with a side ratio of one to several times, or practically one to ten times, or preferably three to five times. If the side ratio exceeds 20 times, it is closer to the conventional flow cell, and hard to manufacture and likely to be broken.

In this apparatus, the sheath liquid for leading the sample into the measuring range c, while enveloping it from the surrounding is passed into the flow cell 10, and at the same time the sample is passed into the sheath liquid from the nozzle 12, so that the thickness of the sample flow is reduced (throttled) to a specific value (about the thickness of the particles to be measured, for example, about 10 μm when measuring erythrocytes in blood sample).

The width, a1, of one side of lead-in passage 14 (see FIG. 2, FIG. 4) is constant, for example, at 1 mm, so that the width of the sheath liquid flow may not change near the front end of the nozzle 12, so that a reducing action is not exerted on the sample flow in the direction of the width a1.

On the other hand, the width, b1, at the other side of the lead-in passage 14 (see FIG. 3, FIG. 4) is, different from the case above, gradually narrowed as it approaches the measuring passage 16 to a final width, b2, (see FIG. 3, FIG. 4), so that a reducing action is exerted on the sample flow. The width, b1, is, for example, 10 mm, and the width, b2, is, for example, 0.5 mm.

By disposing a conventional circular hole nozzle in the flow cell 10, the sample flow may be formed like a sheet or board, that is, a wide sample flow with a thickness of about 10 μm may be formed. In this method alone, however, a sample flow having a sufficient width for the measuring range of the imaging flow cytometer cannot be prepared.

Accordingly, by using the sample nozzles as shown in FIG. 5 to FIG. 15, the thickness of the sample flow flowing in the measuring passage 16 of the flow cell 10 may be further reduced to form a flat flow. This is described in detail below.

The imaging region is basically determined by the scale factor (magnification) of-the objective lens (not shown) and the size of the image pickup device of the video camera (not shown). For example, in the case of an objective lens with a scale factor of 10 times and a video camera CCD (changed coupled device) image pickup device of ⅔ inch, since the size of the light receiving surface of the CCD element is 8.8×6.6 mm, the imaging region in the flow cell 10 is 0.88×0.66 mm, or when the objective lens has a scale factor of 40 times, the imaging region is 0.22×0.165 ram, and therefore if the scale factor of the objective lens is 10 times, a sample flow width of 0.9 mm may be sufficient.

In the sheath flow measuring method, the sectional area of the sample flow running in the flow cell is determined by the flow rate ratio of the sample flow and sheath liquid flow. For example, using a conventional circular hole nozzle having only one sample flow outlet, if the sample discharge per unit time is 2.6 μl/sec and the flow rate of sheath liquid is 500 μl/sec, in the section of the measuring passage 16 of the flow cell, the area ratio occupied by the sample flow and sheath liquid is 1:187. Accordingly, as shown in FIG. 2 to FIG. 4, supposing the sectional area of the measuring passage 16 to be 1 mm×0.5 ram, the area occupied by the sample flow is 1/187 of 0.5 mm$^2$ that is $2.7 \times 10^{-3}$ mm$^2$ Suppose the sample flow can be reduced to 1/20 in one direction only. The value of 1/20 is determined by the shape of the flow cell.

In the conventional circular opening nozzle, if the diameter of the sample flow right after being discharged therefrom is, for example, 0.2 mm, the thickness of the sample flow in the measuring region, c, is 1/20, that is, reduced to 10 μm.

Comparing this result with the result of the area occupied by the sample flow in the measuring passage 16 mentioned above, the size of the region occupied by the sample is obtained as 0.01 mm×0.27 mm. The diameter of the flat flow is 0.27 mm, which is found to be only about ⅓ of the desired imaging region width of 0.9 mm.

To solve this problem, it may be possible to
(a) to increase the sample discharge volume three times; or
(b) to increase the opening area of sample discharge port three times (without changing the flow rate).

However, plan (a) has the following problems. That is, the area occupied by the sample flow in the measuring passage 16 is increased three times from the initial area. On the other hand, the diameter of the sample flow right after discharge from the nozzle is $\sqrt{3}$ times the initial value (three times in area). Hence, if reduced to 1/20, the thickness of the sample flow is $\sqrt{3}$ times the initial value. Accordingly, the width of the sample flow is $3/\sqrt{3} = \sqrt{3}$ times, and substantially both the thickness and width of the sample flow is $\sqrt{3}$ times, and therefore only the thickness cannot be increased three times while keeping the initial thickness.

With plan (b), the following problems are present. That is, the area occupied by the sample flow in the measuring passage 16 is unchanged. The opening area of the nozzle discharge port is 3 times ($\sqrt{3}$ times in diameter), and hence the diameter of the sample flow right after discharge is $\sqrt{3}$ times. Hence the thickness of the sample flow is $\sqrt{3}$ times, and the width of the sample flow is, to the contrary, $1/\sqrt{3}$ times.

In plan (a), moreover, it may also be considered to increase the sheath liquid flow rate three times, but it involves the following problems. That is, the area occupied by the sample flow decreases to be one times, the thickness of the sample flow decreases to be one times, and the width of the sample flow is also one times.

Besides, by varying combinations the sample discharge, volume, sample discharge opening, and sheath liquid flow rate may be considered, but in any case it is not possible to obtain a sufficient flatness.

To solve the above problems, the present invention is intended to enhance the flatness of the sample flow further, by using a nearly elliptical sample discharge port as shown in FIG. 5 to FIG. 10, or a sample nozzle having multi-hole sample discharge ports arranged in one row as shown in FIG. 11 to FIG. 15.

As mentioned above, if the passage reducing rate is 1/20 times, the diameter of the discharge aperture of the nozzle front end is 0.2 mm, the flow rate of sheath liquid per unit time is 500 μl/sec, and the sample flow rate is 2.6 μl/sec, the sectional area of the sample flow in the measuring region is 10 μm×270 μm. To pass the sample in the entire imaging region, it is necessary to discharge the sample approximately 3.3 times more per unit time, that is, more than 8.6 μl/sec.

Figure 9:
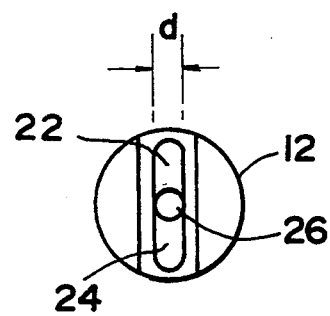
FIG. 9 is a left side view of the nozzle shown in FIG. 6.

In the sample nozzle 12 shown in Fig..5 to FIG. 9, the width d, (see FIG. 9) in the thicknesswise direction in the sample discharge port 22 at the nozzle front end is, for example, kept at 0.2 mm, and the length of the discharge port 22 is, for example, 3.3 times or 0.66 mm.

In FIG. 5 to FIG. 9, for example, a taper 24 is disposed for a specific length from the front end of the nozzle 12, and a nearly elliptical discharge port 22 is formed, but it does not matter if a step form is provided instead of the taper form. Numeral 26 denotes a sample flow inlet.

As shown in FIG. 9, supposing the central part of the nearly elliptical discharge port 22 and the sample flow inlet 26 to be present on the same straight line, it is hard to divide the flow uniformly, and therefore it is desired to shape the discharge port as shown in FIG. 10, that is, the width of the end portion 28 should be slightly broader than the width of the central part.

Figure 12:
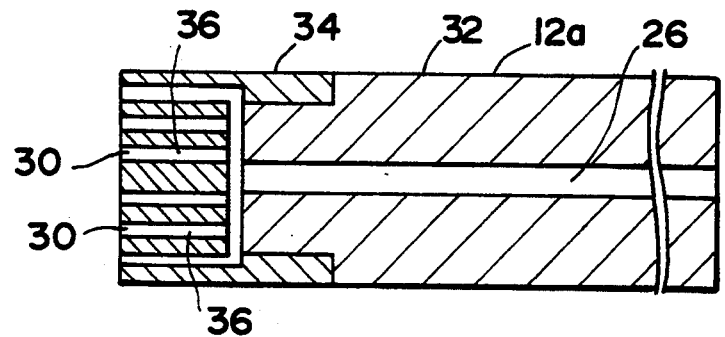
FIG. 12 is a sectional view showing a cut off along the arranging direction of plural small discharge ports in the nozzle shown in FIG. 11.
Figure 13:
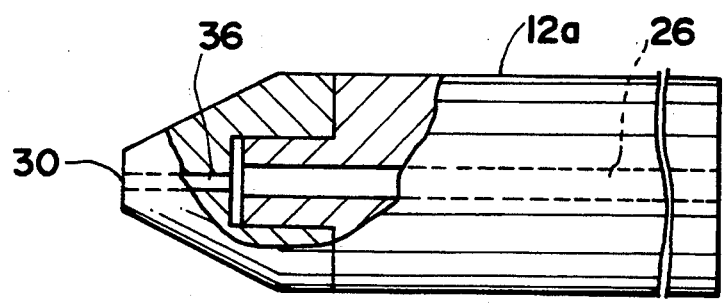
FIG. 13 is a partially cut-away front view of the nozzle shown in FIG. 12 rotated by 90 degrees.
Figure 14:
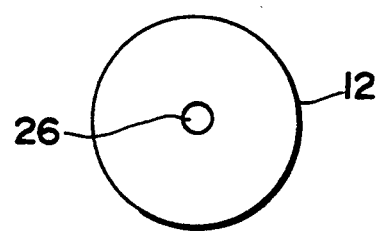
FIG. 14 is a right side view of the nozzle shown in FIG. 12.
Figure 15:
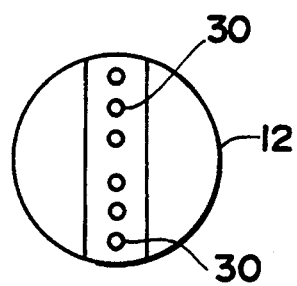
FIG. 15 is a left side view of the nozzle shown in FIG. 12.

In FIG. 11 to FIG. 15, another example of a sample nozzle 12a is shown. In the sample nozzle 12a of this case, for example, the flow rate per unit time is increased 3.3 times by arranging several holes of 0.2 mm in a row, and a sample flow of 10 μm×270 μm is formed per hole, so that it is enough at a maximum to form three or more holes of 0.2 mm at every pitch of 0.27 mm. However, as shown in FIG. 12, when multiple holes are arranged in a comb form, if there are discharge ports on the same straight line as the original sample flow inlet 26, it is hard to divide the flow uniformly, and therefore it is desired to dispose four or six small discharge ports 30 symmetrically to the original sample flow inlet 26. Moreover, in order to make the flow rate from each small discharge port 30 uniform, the central holes may be smaller (for example, 0.15 mm), and the outside holes may be larger (for example, 0.25 mm). This method, however, differs with the number of holes opened in the nozzle front end, and the hole diameter may not always be as specified herein.

In FIG. 12, the sample nozzle 12a is, for example, composed of a main body member 32 and a front end member 34. The main body member 32 has one sample flow inlet 26, and the front end member 34 has, for example, six small passages 36 arranged horizontally in one row. The main body member 32 and front end member 34 are bonded so that the passages may mutually communicate and be formed into one body.

Figure 5:
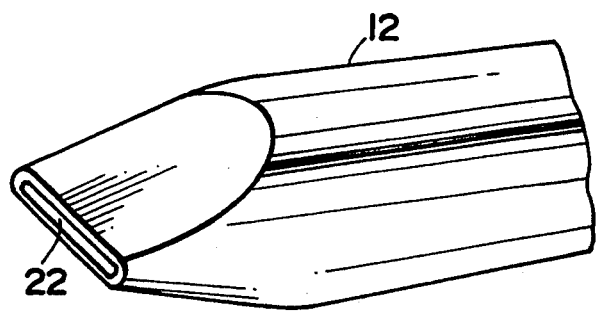
FIG. 5 is a perspective view showing an example of sample nozzle used in the apparatus of the present invention.
Figure 6:
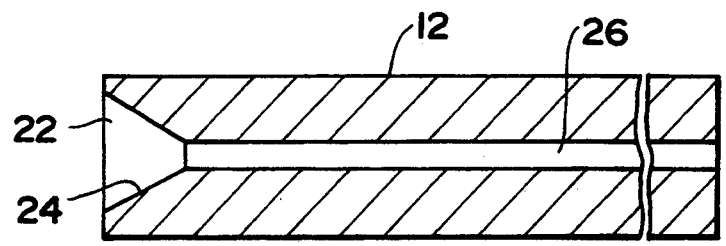
FIG. 6 is a sectional view showing a cut off section along the longitudinal direction of a nearly elliptical discharge port in the nozzle shown in FIG. 5.
Figure 7:
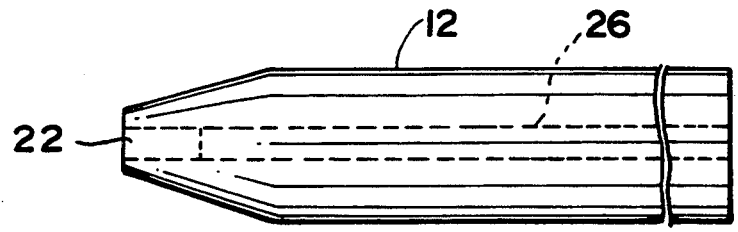
FIG. 7 is a front view of the the sample nozzle shown in FIG. 6 rotated by 90 degrees.
Figure 8:
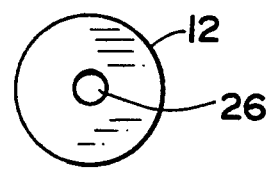
FIG. 8 is a right side view of the nozzle shown in FIG. 6.

In order to dispose plural small discharge ports at the front end of the sample nozzle, aside from the construction above, it may also be possible to insert plural small pipes into the nearly elliptical discharge port 22 shown in FIG. 5, or install plural partitions in the discharge port 22. The shape of the small discharge ports may be, aside from circle, quadrangle, polygon or other shape.

The present invention explained in FIG. 2 to FIG. 15 is thus composed, and hence brings about the following effects.

(1) Not only the lead-in passage is narrowed in one direction, but also the discharge port of the sample nozzle front end is formed in a flat elliptical form or as multiple holes, and therefore a flat sample flow may be easily formed in a rectangular passage with an aspect ratio of one to several times, or a nearly circular measuring passage, if not in the flat measuring passage as in the prior art.

(2) Since the passage of the flow cell may be formed as nearly a square or circle, it is easy to manufacture the flow cell, and its strength may be enhanced. Hence, the manufacturing cost may be reduced, and damages decreased.

FIG. 16 to FIG. 18 relate to another embodiment of an apparatus for forming a flattened sample flow according to the present invention. This apparatus comprises a flow cell 10 for forming a sheath flow, a sample nozzle 12 which is a thin pipe for discharging sample, and a sheath liquid dividing means 13 for dividing the sheath flow symmetrically into two flows.

The flow cell 10 is made of a transparent material such as glass, acrylic and other resin, and comprises a gradually narrowing lead-in passage 14, a narrow measuring passage 16 contiguous to the lead-in passage 14, a sheath liquid feed port 18 disposed in the lead-in passage 14, and a discharge port 20 disposed at the downstream side of the measuring passage 16. Incidentally, a denotes the measuring region. The cross section of the measuring passage 16 is rectangular, with a side ratio of one to several times, or practically one to ten times, or preferably three to five times. If this side ratio exceed 20 times, it is closer to the conventional flow cell, which is hard to manufacture and is likely to be damaged.

In FIG. 18, C1 is a sample discharge means such as a syringe, C2 is a sample liquid tank, and V1, V2 are valves.

In measuring, first valves V1, V2 are opened, and the sample liquid is led to the nozzle 12. Next, the valves V1, V2 are closed, and the syringe C1 is operated, so that the sample is discharged from the nozzle 12 by a specific volume.

The sheath liquid dividing means 13 is composed of, for example, a plate 15 which contacts the sample nozzle 12 and projects in the lateral direction, and a wedge part 17 formed consecutively on the upper part of the plate 15.

In the apparatus of the present invention, for example, by using the sample nozzle as shown in FIG. 5 to FIG. 15 above, the thickness of the sample flow running in the measuring passage 16 of the flow cell 10 may be further formed in a thinner flat flow.

In the sample nozzle 12 shown in FIG. 5 to FIG. 9, the taper 24 is formed for a specific length from the front end of the nozzle 12, and the nearly elliptical discharge port 22 is fabricated, but instead of the taper, a step form may be formed. Numeral 26 denotes a sample flow inlet. In FIG. 9, meanwhile, the shorter diameter d of the nearly elliptical discharge port 22 is, for example, about 0.2 mm.

FIG. 11 to FIG. 15 represent another example of the sample nozzle 12a. In this sample nozzle 12a, for example, several holes of about 0.2 mm are arranged in a row, and hence the flow rate per unit time is increased. However, as shown in FIG. 12, when multiple holes are disposed in a comb form, if the discharge ports are present on the same straight line as the original sample flow inlet 26 at the passage branching portion, it is hard to divide the flow uniformly, and hence it is desired to open four or six small discharge ports 30 symmetrically to the original sample flow inlet 26. Furthermore, to make the flow rate from each small discharge port 30 uniform, the central hole may be smaller (for example, about 0.15 mm), and the outside holes may be larger (for example, about 0.25 mm). This method, however, differs with the number of holes opened in the nozzle front end, and the hole diameter is not always equal to this size.

In the flow cell 10, as shown in FIG. 18, there are several portions shown for controlling the sheath liquid, that is, sheath flow stabilizing portion A, sheath flow dividing portion B, and sheath flow converging portion C.

Figure 19:
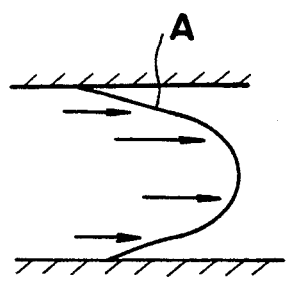
FIG. 19 is an explanatory diagram showing a flow velocity distribution in a conventional sheath flow portion without sheath liquid dividing means (the sheath flow stabilizing portion in the apparatus of the present invention).

The sheath liquid flows in from the sheath liquid feed port 18 in the upper part of the flow cell, and is decelerated in the sheath flow stabilizing portion A to be formed into a laminar flow. For example, supposing the inside diameter of the sheath flow stabilizing portion A to be 10 mm, the flow velocity to be 6.3 mm/sec, the viscosity to be $\mu = 1.002$, and the density to be $\rho = 998$ kg/m$^3$, the Reynolds number Re is about 0.063, which satisfies the laminar flow condition. At this time, the flow velocity distribution is a parabolic profile as shown in FIG. 19.

Figure 20:
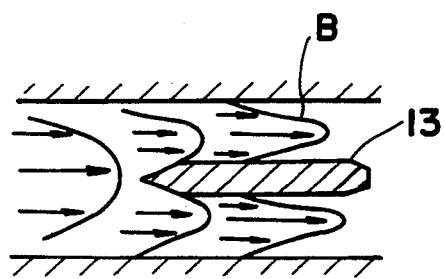
FIG. 20 is an explanatory diagram showing the flow velocity distribution in the sheath liquid dividing portion in the apparatus of the present invention.

Afterwards, the sheath flow is divided into two flat flows by the dividing portion B. In the dividing portion B the sheath liquid dividing means 13 is formed into a proper shape (for example, wedge shape) at its front part, so that the sheath liquid is divided into two flat flows as shown in FIG. 20, while keeping the flow in a laminar state.

Figure 21:
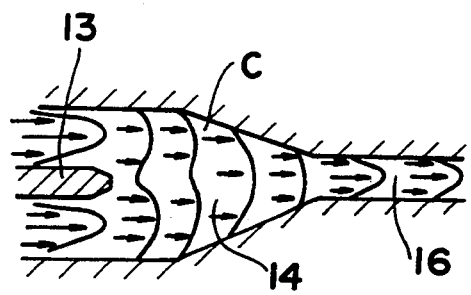
FIG. 21 is an explanatory diagram showing the flow velocity distribution in the sheath liquid converging portion in the apparatus of the invention.

At, in the rear portion of the sheath liquid dividing portion 13, the flow is converted into two flat flows, as shown in FIG. 21, the flow velocity profile is formed in three layers, in which the flow velocity is slow in the central portion, and fast at in the both sides. This flow runs into the measuring passage 16 as shown in FIG. 21, while finally changing into one flow having a parabolic flow velocity profile.

Accordingly, by disposing the sample discharge port of the nozzle 12 in the rear portion of the sheath liquid dividing means 13, that is, in the portion where the flow velocity is the lowest, when the sample is discharged, the sample forms a sandwiched flow being held by the two flat flows of the sheath liquid.

This sandwich flow is later compressed by the taper part of the lead-in passage 14, and runs into the measuring region while keeping the three-layer sandwich structure.

Figure 22:
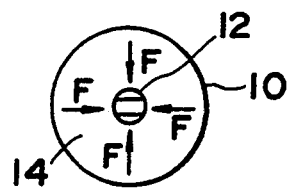
FIG. 22 is an explanatory diagram showing the direction of force applied by the sheath flow to the sample flow in the conventional flow cell, being a plan view as seen from the flow direction of the sheath flow.

In the conventional method not utilizing the sheath liquid dividing means, as shown in FIG. 19, the flow velocity distribution is parabolic and symmetric in rotation with respect to the flow direction, and the sample discharged from the front end of the nozzle 12 receives a compressive pressure F from all vertical directions to the flow direction as shown in FIG. 22, and the flat flow gradually converges on one point.

Figure 23:
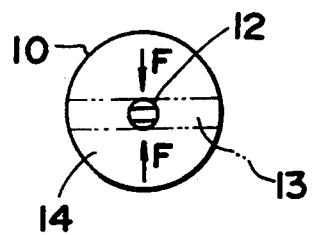
FIG. 23 is an explanatory diagram showing the direction of force applied by the sheath flow to the sample flow in the flow cell of the present invention, being a plan view as seen from the flow direction of the sheath flow.
Figure 24:
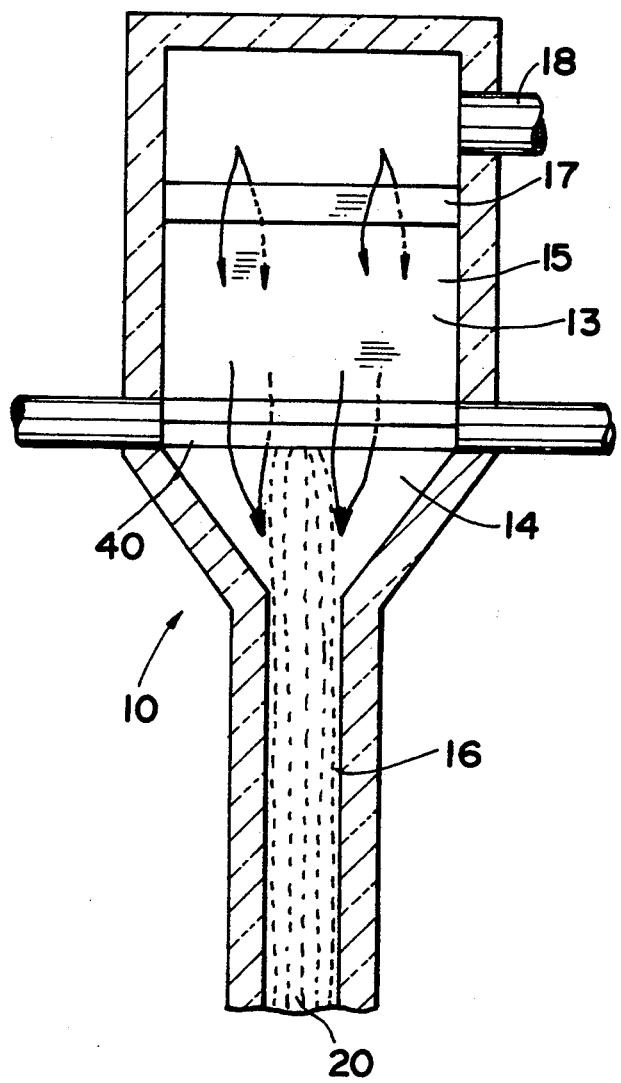
FIG. 24 is a front sectional view showing a further different embodiment of the apparatus of the present invention.
Figure 25:
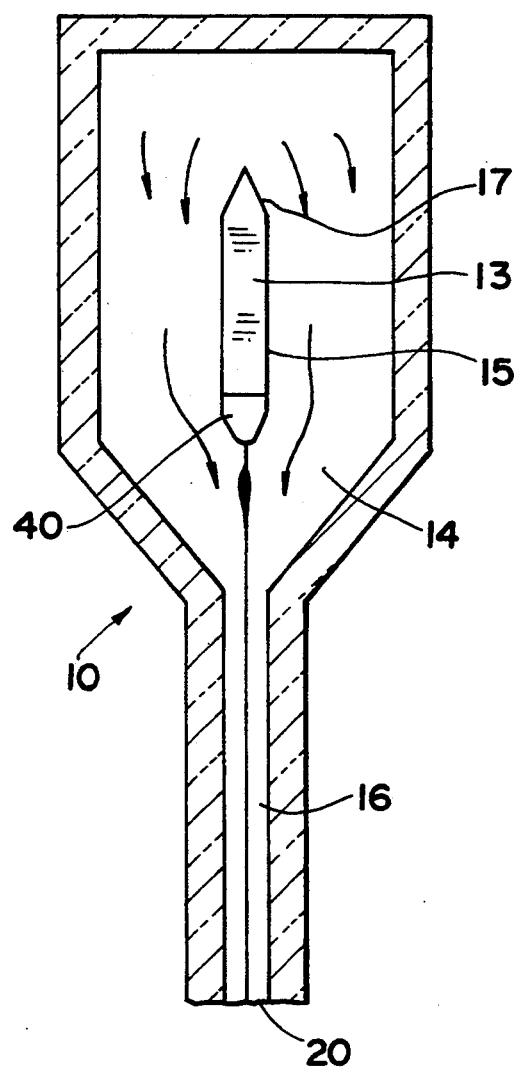
FIG. 25 is a right sectional view of the apparatus shown in FIG. 24.
Figure 26:
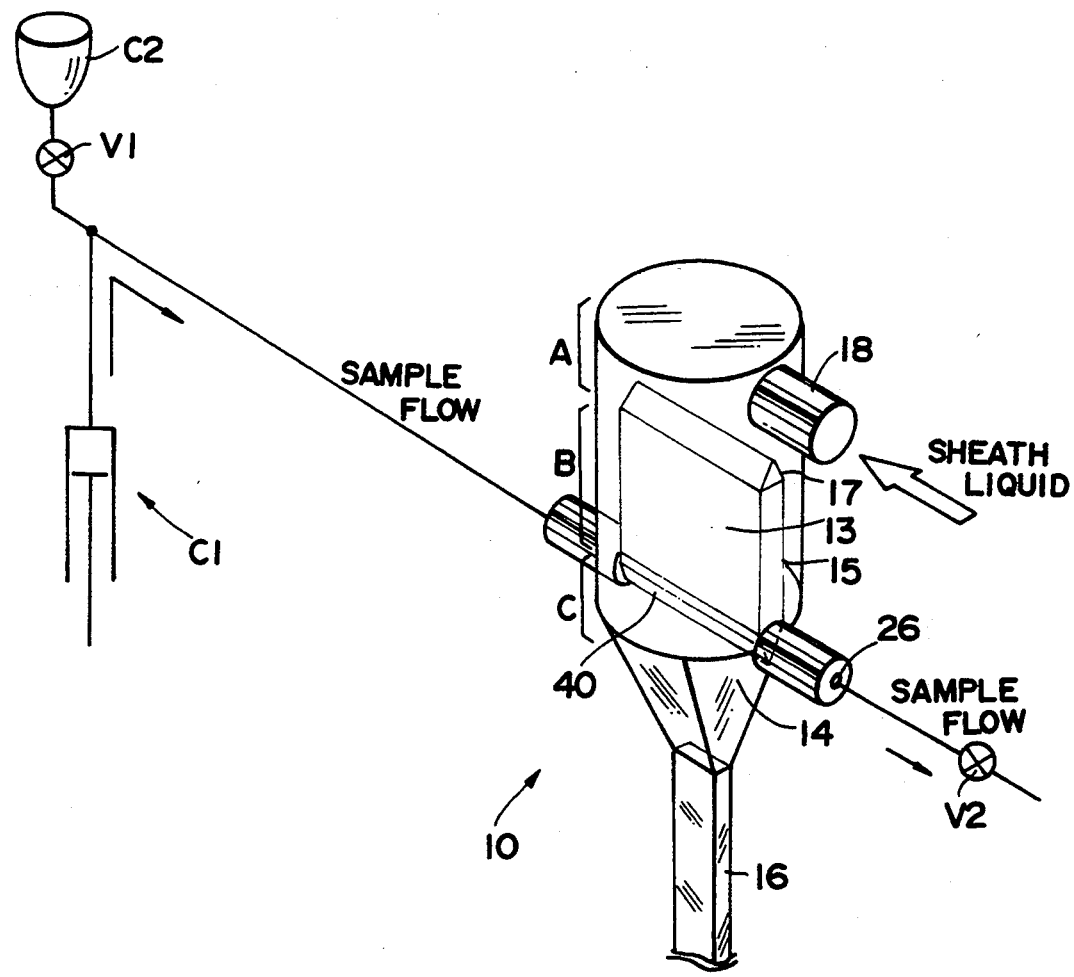
FIG. 26 is a perspective view around the apparatus shown in FIG. 24.

By contrast, in the apparatus of the present invention having the sheath liquid dividing means 13, the sample discharged from the front end of the nozzle 12 is sandwiched by two sheath liquid flat flows, and therefore receives the compressive force F only from the vertical direction (or lateral direction) as shown in FIG. 23, so that a stable flat sheath flow may be obtained.

Besides, by inserting the sheath liquid dividing means 13, the converging position of two flat flows is determined automatically, and if the front end of the nozzle 12 is put at a slightly deviated position from the flow direction, its effect on the thickness of the sample flow in the measuring region is small, and the front end position of the sheath liquid dividing means 13 becomes a guideline for mounting the nozzles, so that the nozzle may be mounted easily.

Thus, by forming the sheath flow stabilizing portion A and dividing portion B in the flow cell 10 and also the converging portion C for joining two flat flows, a stable flat sheath flow may be formed. Meanwhile, the sheath liquid dividing means 13 may be disposed in the lead-in passage 14 so as to envelope, nearly in contact, the sample nozzle 12, or may be directly mounted on the sample nozzle 12.

Another embodiment of the present is explained while referring to FIG. 24 to FIG. 32. In this embodiment, a sample nozzle 40 is disposed at the rear end of the sheath liquid dividing means 13, and the sample nozzle 40 is positioned vertically in the flow direction of the sheath liquid. The method of forming a flat sheath flow is the same as in the foregoing embodiment, and its explanation is omitted herein.

In the apparatus shown in FIG. 16 to FIG. 18, the position of the sample liquid drawn in and held before the start of a measurement, that is, the distance from the branching point above the nozzle and the front end of the nozzle 12 is long, and before the start of a measurement, the inside of the nozzle is filled with a cleaning liquid, so that it was necessary to discharge a large volume of sample from the nozzle (about ten times the sample volume to be measured) until the concentration of sample discharged from the nozzle discharge port reaches a stable concentration (normal sample concentration). Accordingly, a waiting time of 5 to 10 seconds was necessary from the start of feeding a sample into the nozzle until the measurement was actually started.

In this embodiment, in order to shorten the distance from the holding position of the sample liquid to be used in a measurement to the sample discharge port of the nozzle, the inside of the nozzle is filled with sample before filling with sample in the step before measurement, and when the sample is discharged from the sample discharge port of the nozzle, measurement is started at the same time.

In measuring, first valves V1, V2 are opened, and the sample liquid is led nearly to the nozzle 12. Next, the valves V1, V2 are closed, and the syringe C1 is operated, so that the sample is discharged from the nozzle 12 by a specific volume.

Figure 27:
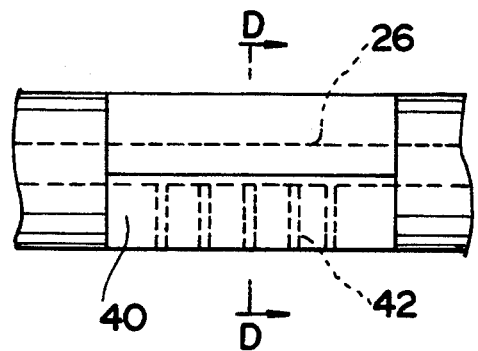
FIG. 27 is a magnified view showing an example of the sample nozzle shown in FIG. 24.
Figure 28:
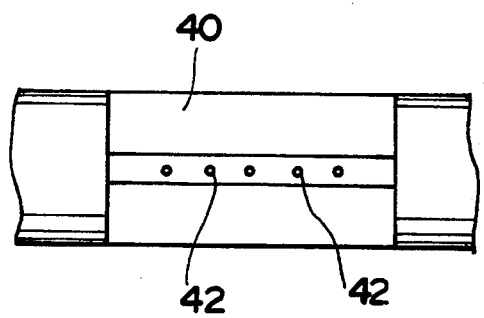
FIG. 28 is a bottom view of the sample nozzle shown in FIG. 27.
Figure 29:
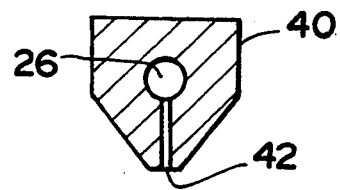
FIG. 29 is a sectional view along the line D—D in FIG. 27.

More specifically, as shown in FIG. 24 to FIG. 27, in the lead-in passage 14, the sample nozzle 40 is disposed across the flow of the sheath liquid. In the lower surface of the sample nozzle 40, as shown in FIG. 27 to FIG. 29, a plurality of small discharge ports 42 are disposed to open toward the measuring passage 16. The small discharge ports 42 communicate with the sample flow inlet 26 of the sample nozzle.

At the upstream side of the small discharge ports 42 of the sample nozzle 40, the sheath liquid dividing means 13 is disposed so as to contact the sample nozzle 40. The lateral projecting direction of the sheath liquid dividing means 13 and the axial direction of the sample nozzle 40 are identical.

Moreover, instead of disposing a plurality of small discharge ports 42 in the sample nozzle 40, as shown in FIG. 30 to FIG. 32, a flat discharge port 44 may be disposed in the sample nozzle 40.

The other constitution and action are the as in the foregoing embodiment.

The invention explained in FIG. 16 to FIG. 32 is thus constructed, and brings about the following effects.

(1) By disposing sheath liquid dividing means projecting in the lateral direction at the upstream side of the sample discharge port, and dividing the sheath liquid into two flows and joining them again, the sample is enveloped with sheath liquid in a sandwich form, so that a flat sample flow may be formed without using a passage flowing a large aspect ratio as in the prior art. Thus, the passage may be close to a square, and the manufacturing cost is reduced, and the risk of breakage is elimianted.

(2) By flattening the discharge port of the sample nozzle or disposing a plurality of the discharge ports horizontally in one row, a more favorable flattened sample flow may be formed.

(3) When disposing the sample nozzle across the lead-in passage, the route to the discharge port may be shorter, and hence the sample discharge preparation time may be cut short. At the same time, contamination between samples may be decreased, and the volume of sample to be prepared may be saved.

Having described preferred embodiments of the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. An apparatus for forming a flattened sample flow for analyzing particles, comprising:

a flow cell having a lead-in passage, a measuring passage contiguous to said lead-in passage, a sheath liquid feed port disposed to supply sheath liquid to said lead-in passage, a sample nozzle for discharging a sample from a sample discharge portion to said measuring passage, disposed across the flow of the sheath liquid in said lead-in passage, and a liquid discharge port for discharging liquid from said measuring passage;

sheath liquid dividing means disposed at the upstream side of said sample nozzle in contact with the sample nozzle so as to divide the sheath liquid symmetrically into two flows, wherein:

the cross section of said measuring passage is rectangular, and the ratio of the width of the long axial direction of said measuring passage to the width of the short axial direction of said measuring passage is in the range of 1 to 10;

said sample nozzle having an inner passage passing through said sample nozzle in the direction of said sample nozzle axis;

the sample discharge portion of the sample nozzle is composed of a plurality of discharge ports communicating with said inner passage;

the plurality of discharge ports are disposed midway of the sample nozzle and arranged in a row in the direction of the sample nozzle axis;

the direction at which said discharge ports are arranged coinciding with the long axial direction of said measuring passage; and said sheath liquid dividing means is disposed so that the lateral projecting direction of said sheath liquid dividing means and the axial direction of the sample nozzle coincide.

2. An apparatus for forming a flattened sample flow for analyzing particles, comprising:

a flow cell having a lead-in passage, a measuring passage contiguous to said lead-in passage, a sheath liquid feed port disposed to supply sheath liquid to said lead-in passage, a sample nozzle for discharging a sample from a sample discharge portion to said measuring passage, disposed across the flow of the sheath liquid in said lead-in passage, and a liquid discharge port for discharging liquid from said measuring passage; and sheath liquid dividing means disposed in contact with said sample nozzle, for dividing the sheath liquid into two symmetrical flows, at the upstream side of the sample nozzle, wherein:

the cross section of said measuring passage is rectangular, and the ratio of the width of the long axial direction of said measuring passage to the width of the short axial direction of said measuring passage is in the range of 1 to 10;

said sample nozzle having an inner passage passing through said sample nozzle in the direction of said sample nozzle axis;

the sample discharge portion of the sample nozzle is composed of a rectangular discharge port communicating with said inner passage;

the rectangular discharge port is disposed midway of said sample nozzle so as to open toward said measuring passage, so as to coincide the long axial direction of the rectangular discharge port with the long axial direction of said measuring passage; and said sheath liquid dividing means is disposed so that the lateral projecting direction of said sheath liquid dividing means and the axial direction of the sample nozzle coincide.

* * * * *